US00PP23008P2

(12) United States Plant Patent
Bergman

(10) Patent No.: US PP23,008 P2
(45) Date of Patent: Sep. 4, 2012

(54) ***CHRYSANTHEMUM* PLANT NAMED 'CIDZ0002'**

(50) Latin Name: *Chrysanthemum×morifolium*
Varietal Denomination: CIDZ0002

(75) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/136,636

(22) Filed: Aug. 5, 2011

(51) Int. Cl.
*A01H 5/00* (2006.01)

(52) U.S. Cl. ..... Plt./287

(58) Field of Classification Search ..... Plt./287
See application file for complete search history.

*Primary Examiner* — Kent L Bell
(74) *Attorney, Agent, or Firm* — Joshua L. Price

(57) ABSTRACT

A new *Chrysanthemum* plant named 'CIDZ0002' particularly distinguished by the very large sized duplex-type inflorescences, quill form-type greyed-purple distinct two-toned ray florets, medium to dark foliage, very strong stems, medium plant vigor and an eight week flowering response.

1 Drawing Sheet

Latin name of the genus and species of the plant claimed: *Chrysanthemum×morifolium.*

Varietal denomination: 'CIDZ0002'.

BACKGROUND OF THE NEW PLANT

The present invention comprises a new *Chrysanthemum*, botanically known as *Chrysanthemum×morifolium*, and hereinafter referred to by the variety name 'CIDZ0002'.

'CIDZ0002' is a product of a planned breeding program. The new cultivar has very large sized duplex-type inflorescences, quill form-type greyed-purple distinct two-toned ray florets, medium to dark foliage, very strong stems, medium plant vigor and an eight week flowering response.

'CIDZ0002' originated from a hybridization made in November 1999 in a controlled breeding environment in Salinas, Calif., USA. The female parent was the proprietary plant designated 'YB-6132', unpatented, with pink ray floret color, decorative spoon-type inflorescences, and a taller more vigorous growth habit.

The male parent of 'CIDZ0002' was an unpatented, proprietary plant identified as 'YB-6606' with bronze-red ray floret color. The resultant seed was sown in July 2000 in Fort Myers, Fla., USA.

'CIDZ0002' was selected as one flowering plant within the progeny of the stated cross in November 2000 in a controlled environment in Fort Myers, Fla., USA.

The first act of asexual reproduction of 'CIDZ0002' was accomplished when vegetative cuttings were propagated from the initial selection in March 2001 in a controlled environment in Fort Myers, Fla., USA.

BRIEF SUMMARY OF INVENTION

Horticultural examination of plants grown from cuttings of the plant initiated in March 2001, and continuing thereafter, has demonstrated that the combination of characteristics as herein disclosed for 'CIDZ0002' are firmly fixed and are retained through successive generations of asexual reproduction.

'CIDZ0002' has not been observed under all possible environmental conditions. The phenotype may vary significantly with variations in environment such as temperature, light intensity and day length.

A Plant Breeder's Right for this cultivar was applied for in Canada on Aug. 17, 2010 (10-7060). 'CIDZ0002' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical inflorescence and foliage characteristics of 'CIDZ0002' with colors being as true as possible with an illustration of this type.

Figure 1:
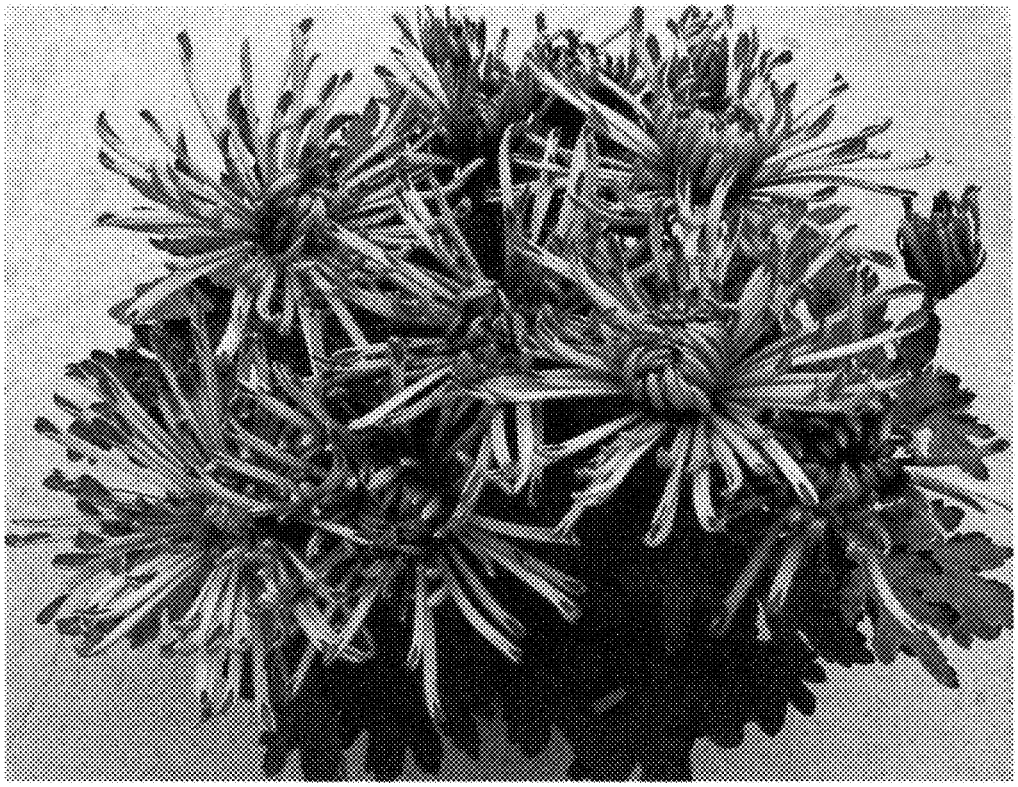
Figure 2:
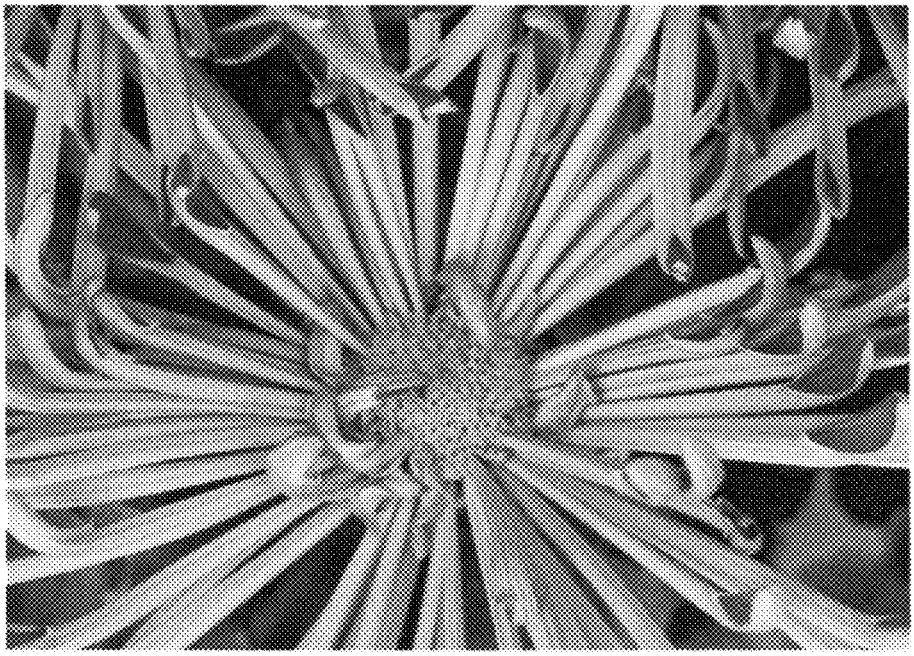

The photographic drawing shows in FIG. 1 four flowering potted plants of the new variety, and in FIG. 2 a close-up of the inflorescence.

DETAILED BOTANICAL DESCRIPTION

The plant descriptions, measurements, and aforementioned photographs were taken in Gilroy, Calif. in early May 2011 under natural light. These plants were propagated and grown in Nipomo, Calif. and shipped to Gilroy, Calif. for the data collection and photographs. These plants were approximately 11 weeks of age; grown as four plants together in a six inch pot under greenhouse trial conditions.

Color references are made to The Royal Horticultural Society Colour Chart (R.H.S.) 2001.

TABLE 1

DIFFERENCES BETWEEN THE NEW VARIETY 'CIDZ0002' AND A SIMILAR VARIETY

| | 'CIDZ0002' | 'Yowinnipeg' (U.S. Plant Pat. No. 16,638) |
|---|---|---|
| Inflorescence diameter: | Larger | Smaller |
| Quantity of ray florets: | Fewer | More |
| Ray floret color: | More greyed-purple | More red-purple |

Plant:
*Form, growth and habit*.—Herbaceous pot-type, stems upright and strong, medium vigor.
*Plant height*.—18.0 cm.
*Plant height* (*inflorescence included*).—24-26.0 cm.
*Plant width*.—12-24.0 cm.
Roots:
*Number of days to initiate roots*.—About 4 days at about 22 degrees C.
*Number of days to produce a rooted cutting*.—About 10-12 days at 22 degrees C.
*Type*.—Fine, fibrous, free branching.
*Color*.—RHS N155B but whiter.
Foliage:
*Arrangement*.—Alternate, simple.
*Immature, leaf color, upper surface*.—Closest to RHS 139A.
*Lower surface*.—RHS 137B.
*Mature, leaf color, upper surface*.—Closest to RHS 139A with some slightly lighter blotching.
*Lower surface*.—RHS 137B.
*Length*.—10-11.5 cm.
*Width*.—7.7-8.3 cm.
*Shape*.—Ovate.
*Base shape*.—Attenuate.
*Apex shape*.—Mucronulate.
*Margin*.—Deeply palmately lobed; irregularly serrate.
*Texture, upper surface*.—Bifid T-shaped hairs.
*Lower surface*.—Bifid T-shaped hairs.
*Color of veins, upper surface*.—RHS 144A.
*Color of veins, lower surface*.—RHS 144A.
*Petiole color*.—RHS 144A.
*Length*.—4.0-4.5 cm.
*Diameter*.—2-3 cm.
*Texture*.—Bifid T-shaped hairs.
Stem:
*Quantity of main branches per plant*.—2-4.
*Color of stem*.—RHS C137C but appears lighter due to hairs.
*Length of stem*.—14-17.0 cm.
*Diameter*.—5-8.0 cm.
*Length of internodes*.—1.5-3.0 cm.
*Texture*.—Bifid T-shaped hairs.
*Color of peduncle*.—RHS 137C but appears lighter due to hairs.
*Length of peduncle*.—About 5.0 cm.
*Peduncle diameter*.—3-4.0 cm.
*Texture*.—Bifid T-shaped hairs.
Inflorescence:
*Type*.—Compositae type, solitary inflorescences duplex-type, borne terminally above foliage, ray florets arranged acropetally on a capitulum.
*Quantity of short days to flowering* (*response time*): About 8 weeks.
*Quantity of inflorescences per plant*.—2-5.
*Lastingness of individual blooms on the plant*.—About 4 weeks.
*Fragrance*.—Slightly spicy.
Bud (just before opening/showing color):
*Color*.—Closest to RHS 186B.
*Length*.—1.4-1.7 cm.
*Width*.—1.3-1.4 cm.
*Shape*.—Oblate.
Immature inflorescence:
*Diameter*.—6-7 cm.
*Color of ray florets, upper surface*.—Between RHS 187C and RHS 187D.
*Lower surface*.—Closest to RHS 186B but darker.
Mature inflorescence:
*Diameter*.—16-18.0 cm.
*Depth*.—2.0 cm.
*Total diameter of 'disc'*.—2.0-2.3 cm.
*Receptacle height*.—0.7-0.8 cm.
*Receptacle diameter*.—1.0-1.1 cm.
Ray florets:
*Average quantity of florets*.—Approximately 100 in several whorls.
*Color of florets, upper surface*.—Between RHS 187C and RHS 187D.
*Lower surface*.—Closest to RHS 186B but darker.
*Length*.—4.5-8.5 cm.
*Width*.—0.35-0.5 cm.
*Shape*.—Quill.
*Apex shape*.—Irregularly emarginate.
*Margin*.—Entire; but mostly fused to form the quill.
*Texture, upper surface*.—Papillose.
*Lower surface*.—Glabrous or papillose.
Petaloids:
*Quantity*.—About 10.
*Length*.—2.0-3.0 cm.
*Width*.—0.2-0.3 cm.
*Color*.—Between RHS 187C and RHS 187D.
Disc florets:
*Average quantity of florets*.—Approximately 100.
*Color of florets*.—Closest to RHS 6C maturing to about RHS 13A.
*Length*.—0.3-0.4 cm.
*Width*.—0.1 cm.
*Shape*.—Tubular, elongated.
*Apex shape*.—Acute, 5 pointed.
Phyllaries:
*Quantity*.—30-35.
*Color, upper surface*.—RHS 138A.
*Lower surface*.—RHS N138C.
*Length*.—0.7-1.4 cm.
*Width*.—0.3-0.4 cm.
*Shape*.—Lanceolate.
*Apex shape*.—Acute.
*Base*.—Fused.
*Margins*.—Entire; papery.
*Texture, upper surface*.—Glabrous.
*Lower surface*.—Bifid T-shaped hairs.
Reproductive organs:
*Pistil*.—1.
*Found on both florets*.—Yes.
*Length*.—0.8-0.9 cm.
*Style color*.—RHS 1B but greener.
*Style length*.—0.7 cm.
*Stigma color*.—RHS 7B.
*Stigma shape*.—Bi-parted.

*Ovary color*.—Not observed.
*Stamens*.—4.
*Found on only disc florets*.—Yes.
*Color of filaments*.—RHS 1C.
*Length filaments*.—0.4 cm.
*Anther color*.—RHS 14C.
*Anther length*.—0.15-0.2 cm.
*Anther shape*.—Oblong.
*Color of pollen*.—RHS 17C.
*Pollen amount*.—Abundant.
*Fertility/seed set*.—Has not been observed on this hybrid.
*Disease/pest resistance*.—Has not been observed on this hybrid.

What is claimed is:

1. A new and distinct variety of *Chrysanthemum* plant named 'CIDZ0002' substantially as illustrated and described herein.

* * * * *

UNITED STATES PATENT AND TRADEMARK OFFICE

CERTIFICATE OF CORRECTION

PATENT NO. : PP23,008 P2
APPLICATION NO. : 13/136636
DATED : September 4, 2012
INVENTOR(S) : Bergman It is certified that error appears in the above-identified patent and that said Letters Patent is hereby corrected as shown below:

At column 3, line 49, delete "RHS C137C" and insert therefor --RHS 137C--

Signed and Sealed this
Ninth Day of October, 2012

David J. Kappos

David J. Kappos
*Director of the United States Patent and Trademark Office*